United States Patent
Czwaluk

(10) Patent No.: US 11,014,056 B2
(45) Date of Patent: May 25, 2021

(54) STIRRER UNIT FOR A FERMENTER IN A BIOGAS PLANT

(71) Applicant: UTS BIOGASTECHNIK GMBH, Hallbergmoos (DE)

(72) Inventor: Andreas Czwaluk, Vechta (DE)

(73) Assignee: UTS BIOGASTECHNIK GMBH, Hallbergmoos (DE)

( * ) Notice: Subject to any disclaimer, the term of this patent is extended or adjusted under 35 U.S.C. 154(b) by 652 days.

(21) Appl. No.: 15/524,066

(22) PCT Filed: Nov. 5, 2015

(86) PCT No.: PCT/EP2015/075828
§ 371 (c)(1),
(2) Date: May 3, 2017

(87) PCT Pub. No.: WO2016/071454
PCT Pub. Date: May 12, 2016

(65) Prior Publication Data
US 2017/0333853 A1    Nov. 23, 2017

(30) Foreign Application Priority Data

Nov. 7, 2014  (DE) .......................... 102014116242.0

(51) Int. Cl.
*B01F 7/00*    (2006.01)
*B01F 7/06*    (2006.01)
(Continued)

(52) U.S. Cl.
CPC ...... *B01F 7/00725* (2013.01); *B01F 7/00733* (2013.01); *B01F 7/00975* (2013.01);
(Continued)

(58) Field of Classification Search
CPC .............. B01F 7/00725; B01F 7/00733; B01F 7/00975; B01F 7/06; B01F 13/1013;
(Continued)

(56) References Cited

U.S. PATENT DOCUMENTS

| 5,458,816 | A | * | 10/1995 | Ebner ................. | B01F 3/04539 |
| | | | | | 261/64.1 |
| 6,793,167 | B2 | * | 9/2004 | Karkos, Jr. ............ | A23G 9/045 |
| | | | | | 241/101.2 |
| 2011/0177558 | A1 | | 7/2011 | Medoff et al. | |

FOREIGN PATENT DOCUMENTS

| DE | 1557076 A1 | 3/1970 |
| DE | 2823238 B1 | 10/1979 |

(Continued)

OTHER PUBLICATIONS

Translation of DE102007022904 by IP.com accessed Aug. 2020 (Year: 2020).*

(Continued)

*Primary Examiner* — William H. Beisner
*Assistant Examiner* — Danielle B Henkel
(74) *Attorney, Agent, or Firm* — Greer, Burns & Crain, Ltd.

(57) ABSTRACT

Agitating device (10) for a digester (1) of a biogas plant (100) having a housing (11) and a driving device (12) for rotatably driving the agitator blades (13-15). The driving device (12) comprises a drive shaft (16) and an electric drive motor (20) wherein the drive motor (20) is accommodated sealed in the housing (11). The drive motor (20) comprises an outer, hollow stator (21) and a rotary rotor (22) which is centrally accommodated therein and is configured at least partially hollow. The rotor (22) is rotatably supported at the housing (11) and comprises a coupling device (23) for non-rotatable coupling with the drive shaft (16) to drive the (Continued)

at least one agitator blade (13-15) by means of the drive shaft (16).

19 Claims, 4 Drawing Sheets

(51) Int. Cl.
    *C12M 1/107*     (2006.01)
    *C12M 3/00*     (2006.01)
    *C12M 1/06*     (2006.01)
    *B01F 13/10*     (2006.01)

(52) U.S. Cl.
    CPC ............ *B01F 7/06* (2013.01); *B01F 13/1013* (2013.01); *C12M 21/04* (2013.01); *C12M 23/46* (2013.01); *C12M 27/02* (2013.01); *B01F 2215/0431* (2013.01); *B01F 2215/0481* (2013.01); *Y02E 50/30* (2013.01)

(58) Field of Classification Search
    CPC .... B01F 2215/0431; B01F 2215/0481; C12M 21/04; C12M 23/46; C12M 27/02; Y02E 50/343
    See application file for complete search history.

(56) References Cited

FOREIGN PATENT DOCUMENTS

| | | |
|---|---|---|
| DE | 3818727 A1 | 12/1989 |
| DE | 3902326 A1 | 8/1990 |
| DE | 4321722 A1 | 1/1995 |
| DE | 19517901 C1 | 10/1996 |
| DE | 19721528 A1 | 11/1998 |
| DE | 19727202 A1 | 1/1999 |
| DE | 29822149 U1 | 4/1999 |
| DE | 10303097 A1 | 8/2003 |
| DE | 202005005165 U1 | 8/2006 |
| DE | 102005017823 A1 | 10/2006 |
| DE | 202006010384 U1 | 11/2006 |
| DE | 102006053339 A1 | 5/2008 |
| DE | 102007022904 * | 11/2008 |
| DE | 202009006223 U1 | 7/2009 |
| DE | 102008010841 A1 | 8/2009 |
| DE | 102009029274 A1 | 3/2011 |
| DE | 102011118204 A1 | 5/2013 |
| DE | 102012021206 A1 | 4/2014 |
| EP | 1895641 A2 | 3/2008 |
| EP | 2096740 A1 | 9/2009 |
| EP | 2272651 A1 | 1/2011 |
| EP | 2270128 A1 | 5/2011 |
| WO | 2007118788 A1 | 10/2007 |
| WO | 2014020544 A1 | 2/2014 |

OTHER PUBLICATIONS

Germany Patent Application No. DE102014116242, Search Report dated Aug. 11, 2015.
International Patent Application No. PCT/EP2015/075828, International Search Report and Written Opinion dated Feb. 12, 2016.
International Patent Application No. PCT/EP2015/075828, International Preliminary Report on Patentability dated May 18, 2017.
European Patent Application No. 15800732, Office Action dated Sep. 25, 2019—A concise explanation of relevance of this non-English document is enclosed.

* cited by examiner

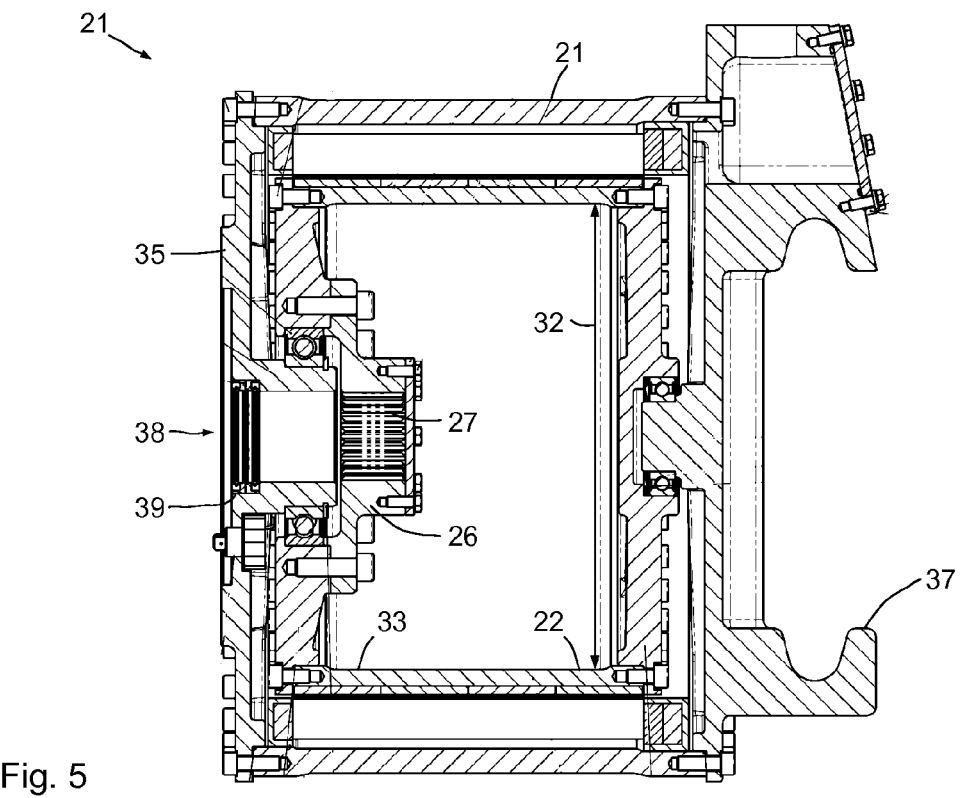
Fig. 5
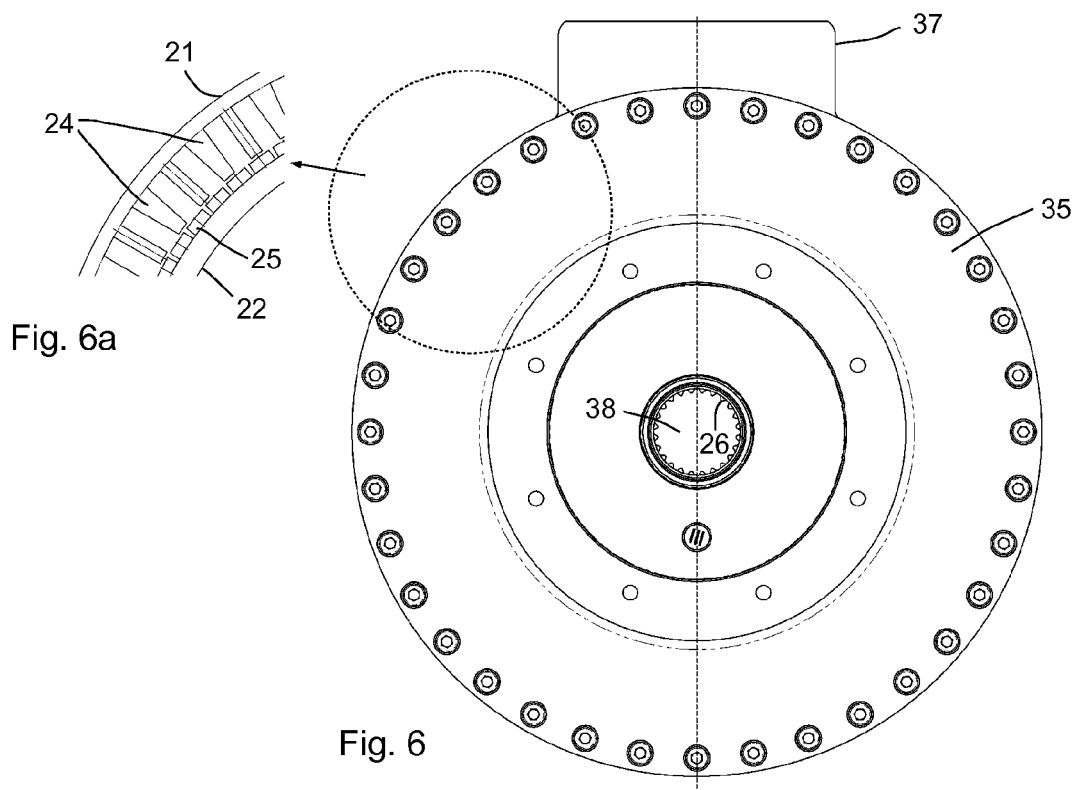
Fig. 6a
Fig. 6

STIRRER UNIT FOR A FERMENTER IN A BIOGAS PLANT

CROSS-REFERENCE TO RELATED APPLICATIONS

This application is a National Stage Entry of International Application No. PCT/EP2015/075828, filed Nov. 5, 2015, which claims the benefit of German Application Serial No. 102014116242.0, filed Nov. 7, 2014.

BACKGROUND

The present invention relates to an agitating device which is in particular but not solely provided for a digester of a biogas plant. Such an agitating device comprises a housing and a driving device for rotatably driving at least one agitator blade of the agitating device. The driving device comprises a drive shaft and a drive motor.

Biogas plants comprise as a rule a digester or a number of digesters into which a substrate is charged to produce biogas. It is necessary to stir or agitate the substrate in the digester interior to obtain and ensure favourable conditions for operating the digester.

Agitators respectively agitating devices are used for stirring, comprising as a rule one or more agitator blade/s for thoroughly mixing the substrate. The prior art has disclosed agitators having a hydraulic drive. These agitators show the advantage that the agitator does not need any electric current for operating within the digester. This is an advantage since the digester interior may contain explosible gas or an explosible gas mixture. However, hydraulic agitators show the drawback that the energy required for operating the agitator needs to be supplied from the outside through hydraulic lines.

Using an agitator having an electric drive motor is simpler in comparison. Although suitable sealing needs to be provided, hydraulic supply lines can be dispensed with. Another drawback of using electric motors is that typical asynchronous motors show a comparatively low rotational force and therefore they are combined with a transmission for operation. This increases the overhead and expenditure and reduces the efficiency degree.

SUMMARY

It is therefore the object of the present invention to provide an agitating device in particular for a digester of a biogas plant and a digester having such an agitating device wherein at least part of the aforementioned drawbacks is overcome.

An agitating device according to the invention is in particular provided for a digester of a biogas plant. The agitating device comprises a housing and a driving device for rotatably driving at least one agitator blade. The driving device comprises a drive shaft and an electric drive motor. The drive motor is accommodated sealed in the housing. The drive motor comprises an outer, hollow stator and a rotatable rotor which is configured at least partially hollow and is centrally accommodated therein. The rotor is rotatably supported at the housing and comprises a coupling device for non-rotatable coupling with the drive shaft to drive the at least one agitator blade by means of the drive shaft.

The agitating device according to the invention has many advantages. A considerable advantage of the agitating device according to the invention consists in the use of an electric drive motor with an outer, hollow stator. An at least partially hollow, rotary rotor is disposed within the hollow stator. In this way the drive motor is provided showing larger dimensions so that the hollow stator with the hollow, rotary rotor centrally accommodated thereat is configured for transmitting high rotational forces. This allows to overcome the drawback from the prior art and the drive motor can be coupled gearless with the drive shaft.

The driving device is configured liquid-tight and gas-tight for use in a digester of a biogas plant. The agitating device is configured and provided to enter into the substrate in the digester interior. The agitating device may comprise a plurality of agitator blades whose number is preferably two, three, four or five or more.

In a preferred specific embodiment the stator is equipped with a plurality of electric windings and the rotor is equipped with a plurality of permanent magnets. The stator may for example be provided with 40-80 toothed coil windings and the rotor, with 40-100 surface magnets. In a preferred configuration 60 windings and 70 surface magnets are employed. The high number of more than ten and in particular more than 20 electric windings and permanent magnets results in good responsivity and in high rotational force which is reliably provided even for low speeds of rotation. It is also possible to use e.g. poles, 35 pole pairs and/or 280 magnets or more.

In a preferred configuration the drive motor is configured as a direct drive and the drive shaft and/or a blade hub is coupled with the drive motor gearless. This configuration is very advantageous since transmission losses due to the transmission can be avoided. Moreover a transmission is a wearing part having a limited service life. The architecture, controls and dimensions of this specific embodiment of the agitating device according to the invention achieve a high degree of efficiency and high reliability.

In a preferred specific embodiment the coupling device of the rotor comprises a tooth flange having an internal toothing to non-rotatably receive the drive shaft equipped with an external toothing. This tooth flange allows to reliably, quickly, and simply couple the drive shaft with the drive motor.

Preferably the driving device comprises an attachment device having at least one bearing device to rotatably support the drive shaft, the attachment device being detachably connected with the housing.

In particular the interaction of the tooth flange and an attachment device with a bearing device for rotatably supporting the drive shaft enables and ensures a simple while reliable architecture of the driving device of the agitating device. Sealing the drive motor against liquids and gases is likewise simpler in construction. The drive shaft enters the housing of the drive motor from one side only so that the drive shaft needs to be sealed in one place only. These configurations allow to screw the attachment device to the housing of the driving device respectively of the drive motor or to attach it thereto in some other way.

In preferred configurations a blade hub is non-rotatably disposed on the drive shaft and the at least one agitator blade is attached to the blade hub.

As a rule the drive shaft is fixedly connected with the blade hub in all the configurations. A configuration is preferred where at least one radial engaging dog on the drive shaft or the blade hub engages in a corresponding groove or a corresponding recess of the blade hub to establish a non-rotatable connection.

In a preferred specific embodiment the blade hub is fixed by means of a fixing unit to the front end of the drive shaft in the axial direction. In simple configurations the fixing unit may take the form of a lid or the like. It is also possible to configure the fixing unit as a sufficiently strong pin or the like. Preferably a rear stopper is provided correspondingly on the drive shaft for the blade hub.

In particularly preferred specific embodiments the external diameter of the blade hub is at least twice and in particular at least three times the size of the external diameter of the drive shaft. The external diameter of the blade hub is understood to mean the diameter without the agitator blades respectively with the agitator blades removed.

Particularly preferably the internal diameter of the hollow portion of the rotor is at least twice the size of the external diameter of the drive shaft. This achieves a particularly large diameter of the force introducing part of the drive motor so that particularly high rotational forces can be transmitted even with slow speeds of rotation.

Particularly preferably the external diameter of the rotor is therefore at least three times and in particular at least four times the size of the external diameter of the drive shaft. This defines a large-dimensioned drive motor which can work gearless so as to save on the costs and structural volume of a transmission. Moreover the efficiency degree increases since an additional component which would involve transmission losses can be omitted.

Preferably the external diameter of the rotor is larger than the external diameter of the blade hub.

In a preferred configuration the drive shaft protrudes from a front face of the housing. Advantageously a console accommodation for attachment to a console is disposed on the rear face of the housing. By means of the console accommodation the housing is attached respectively disposed on a console which console is disposed in particular height-adjustable on a support unit for example having the form of a support rod or the like. The support rod is preferably disposed rotatably to generally allow different heights and orientations of the agitator in the digester.

Preferably the drive shaft extends out of the housing outwardly from the tooth flange through a shaft opening in an end cover. In particular the shaft opening has disposed on it at least one shaft seal between the end cover and the drive shaft. In this way a reliable sealing is achieved already where the drive shaft enters into the housing. This considerably facilitates to achieve the goal of providing an absolutely tight drive motor.

In all the configurations a number of agitator blades may be provided.

The inventive digester of a biogas plant comprises a digester interior that can at least partially be filled with a substrate. At least one agitating device controlled by a control device is disposed in the digester interior. The agitating device comprises a housing, at least one agitator blade and a driving device for rotatably driving the at least one agitator blade. The driving device comprises a drive shaft and an electric drive motor with the drive motor accommodated sealed in the housing. The drive motor comprises an outer, hollow stator and a rotary rotor which is configured at least partially hollow and is centrally accommodated therein. The rotor is rotatably supported at the housing and comprises a coupling device for non-rotatable coupling with the drive shaft to drive the at least one agitator blade by means of the drive shaft.

The digester according to the invention also has many advantages since one or more agitating devices disposed in the digester interior enable reliable, efficient operation.

The rotor is preferably provided inside and the stator surrounds the rotor. The rotor is in particular configured as a hollow shaft.

Particularly preferably the driving device is controlled by a frequency converter. Using two or more frequency converters is also possible.

The drive motor is preferably suitable, given a speed of rotation of 1 revolution/s respectively a speed of rotation of 60 revolutions/min, to apply a torque of at least 250 Nm and in particular at least 300 Nm. A torque of at least 500 Nm at a speed of rotation of at least 120 revolutions/min is typical. The torque may be in excess of 1000 Nm.

In all the configurations the drive motor is in particular configured for speeds of rotation of up to 150 and in particular up to 200 revolutions/min or more. The drive motor is in particular provided for speeds of rotation between 30 and 180 revolutions/min.

In all the configurations the agitating device is in particular automatically height-adjustable and/or side-adjustable.

Further advantages and applications of the present invention can be taken from the exemplary embodiment which will be discussed below with reference to the enclosed figures.

BRIEF DESCRIPTION OF THE DRAWINGS

The figures show in:

FIG. 5a sectional view of the drive motor of the agitating device according to FIG. 4;

FIG. 6a front view of the agitating device according to FIG. 5;

FIG. 6 an enlarged cross-sectional detail from FIG. 6;

DETAILED DESCRIPTION

Figure 1:
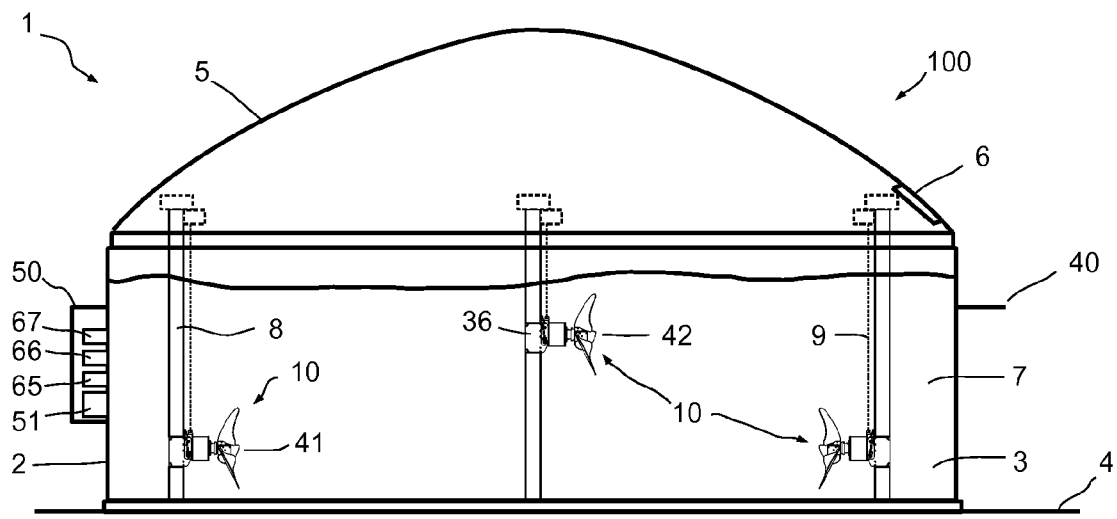
FIG. 1a schematic lateral cross-section of a digester.

Referring to the figures an exemplary embodiment will now be discussed. FIG. 1 shows a simplistic side view of a digester 1 of a biogas plant 100.

The digester 1 is preferably approximately circular in cross section and is presently provided with a circumferential digester wall 2 for example of concrete or steel. The digester roof 5 may be configured as a flat steel or concrete roof, as may the floor. This digester roof 5 is formed by an in particular flexible material, extending upwardly from the wall so that a domed structure of the tank roof 5 is obtained. The inclination angle of the digester roof 5 depends on the specific conditions and may be 15° or more and in particular 30° or 45° or more. Preferably the digester roof 5 is at least partially and in particular entirely removable to render the digester interior 3 accessible. In the digester interior 3 a substrate 7 is provided when in operation.

The digester roof 5 may be provided with at least one servicing opening 6 for example for servicing an agitator 10 disposed in the digester interior 3. A platform 40 may be attached for example to the outside of the digester wall 2 for an operator to stand on.

Figure 2:
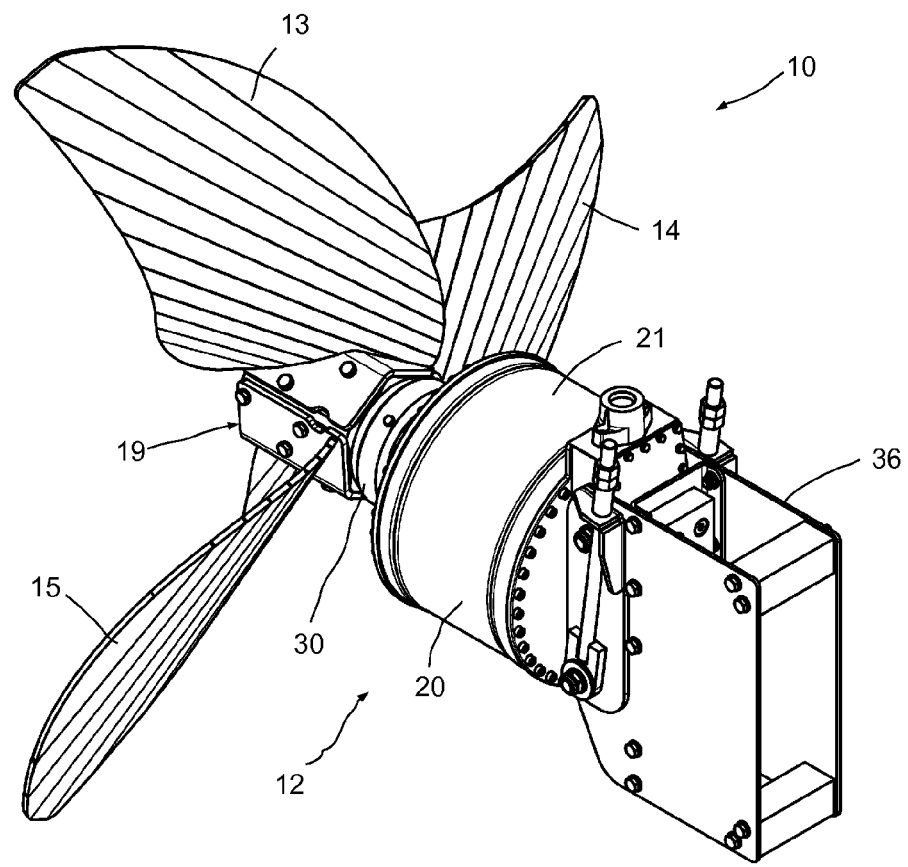
FIG. 2a perspective view of an agitating device for the digester according to FIG. 1.

FIG. 2 shows a schematic perspective illustration of the agitating device 10 with the driving device 12. The agitating device 10 is received height-adjustable on the support unit 8 configured as a support rod by means of a console 36. The agitator 10 is pivotable together with the support unit 8 and may be rotated 360°. This allows to swivel the agitator blades 13, 14 and 15 toward the digester wall 2 and to displace it upwardly for maintenance purposes where the agitating device is then accessible through the servicing opening 6.

As is shown in the FIG. 1, two, three or even more agitating devices 10 may be disposed in the digester interior 3 to thus ensure a reliable and sufficiently thorough mixing of the substrate 7. It is possible to position the various agitating devices 10 at different heights 41, 42, for agitating for example in the lower region of the digester 1 at the height position 41 while an upper region is mixed at the height position 42 so as to disintegrate or avoid floating sludge layers.

Other than the height positions 41 and 42 shown, other height positions are possible, in particular a mid height position between the first height position 41 and the second height position 42.

Preferably at least two agitating devices 10 are provided each being pivotable around the axis of the support unit 8 so as to generate different degrees of thorough mixing and flow directions within the substrate 7. These agitating devices 10 may be oriented in the same direction of circulation or at an angle to one another or in opposite directions of circulation. They can be used at the same height or in different height positions. Each agitating device 10 is controlled either by its own control device 50 or by a control device 50 shared between the agitators respectively agitating devices 10. A frequency converter 51 is provided for selecting.

As is shown in FIG. 2, an agitating device in this exemplary embodiment shows three agitator blades 13, 14 and 15 which are attached to a blade hub 19. The blade hub 19 in turn is non-rotatably fixed to the drive shaft which is not visible in FIG. 2.

The driving device 12 comprises the drive motor 20 and the attachment device 30 which is fixed to the drive motor 20 housing. The drive motor 20 shows a large diameter which is substantially defined by the external diameter of the stator 21. The stator 21 with its outside surface forms part of the housing of the drive motor 20.

Figure 3:
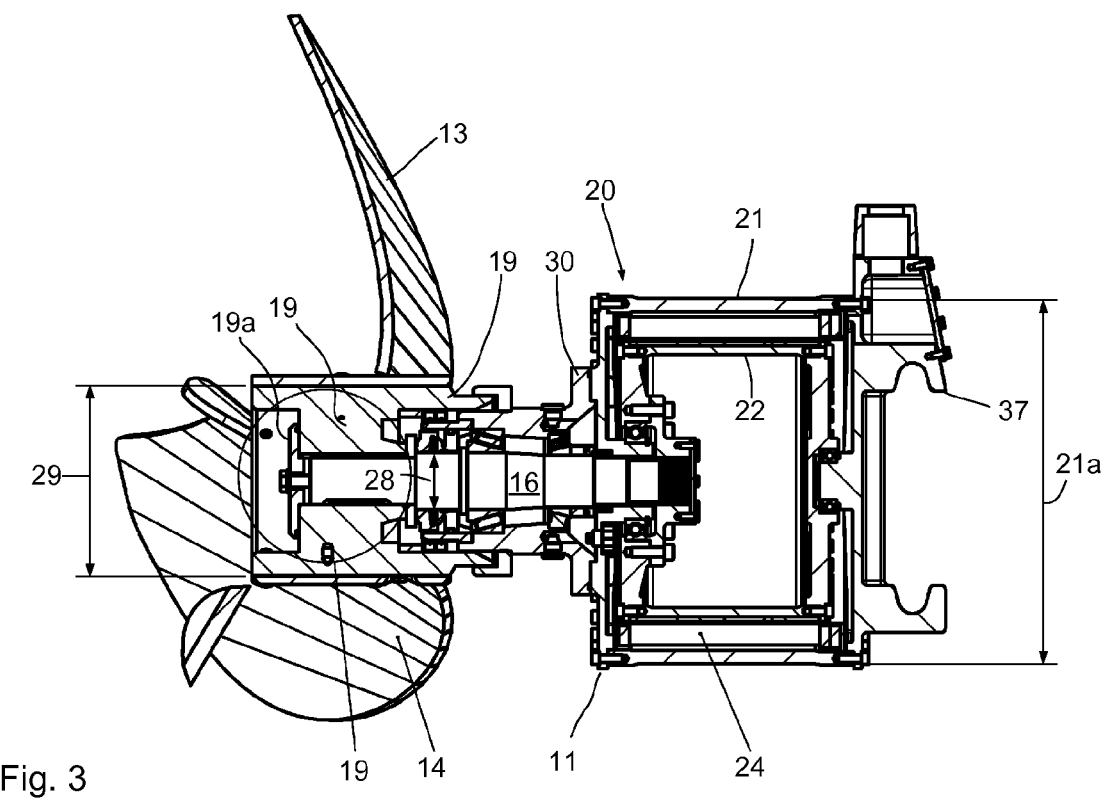
FIG. 3a sectional schematic side view of the agitating device according to FIG. 2.

FIG. 3 shows a sectional schematic side view of the agitating device 10 with the rear agitator blades 13 and 14 visible.

It can be seen that an attachment device 30 is attached to the drive motor 20. The attachment device serves to support and guide the drive shaft 16. The blade hub 19 is attached to the drive shaft 16 to which the agitator blades 13 to 15 are in turn attached. The console accommodation 37 serves for fastening to the console 36. Part of the housing 11 is formed by the stator 21 which shows an external diameter 21a. A hollow rotor 22 is disposed in the interior of the stator 21. The stator 21 shows an external diameter 21a. The drive shaft 16 shows an external diameter 28. The external diameter 21a of the stator is multiple times larger than the external diameter 28 of the drive shaft 16. This achieves a particularly high rotational force of the drive motor 20. Also, an external diameter 29 of the blade hub 19 is considerably smaller than an external diameter 21a of the stator.

Figure 4:
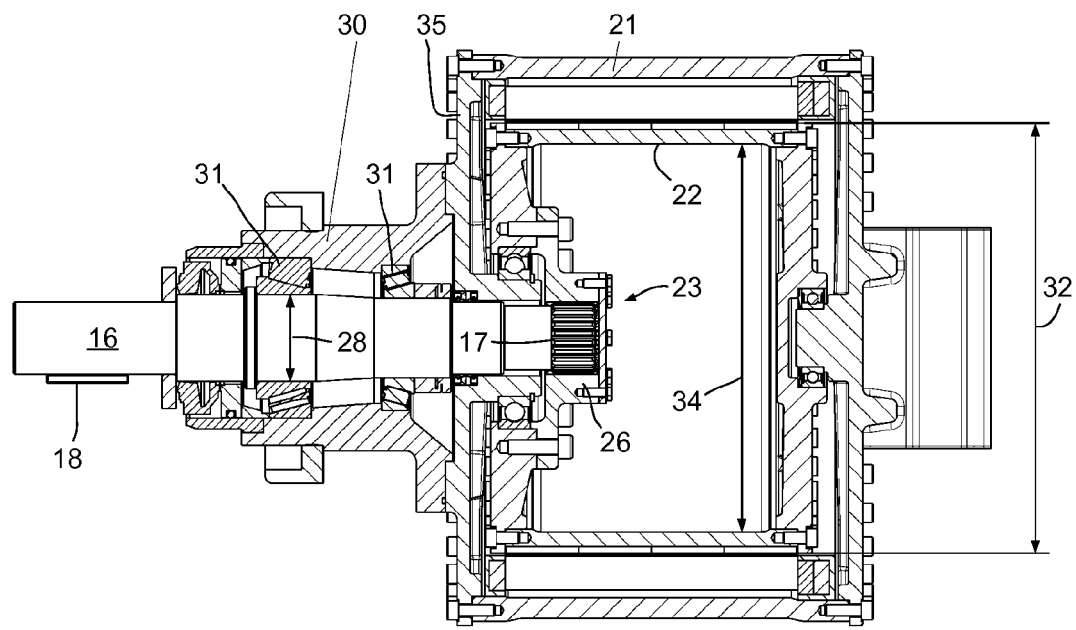
FIG. 4a sectional schematic side view of the agitating device according to FIG. 3 without the agitator blades.

FIG. 4 shows in more detail a cross-section of the drive motor 20 with the attachment device 30 attached thereto. The attachment device 30 is fastened to the end cover 35 of the housing 11 of the drive motor 20. The interior of the attachment device 30 is provided with bearing devices 31 for supporting the drive shaft 16. The drive shaft 16 is provided with an engaging dog 18 which protrudes radially outwardly and enters into a corresponding groove or the like in the blade hub.

The drive shaft 16 is coupled with the rotor 22 via a coupling device 23 which in this instance is configured as a tooth flange 26 and seals the rotor 22 outwardly. The tooth flange 26 shows an internal toothing 27 which when mounted as shown in FIG. 4 is in engagement with the external toothing 17 of the drive shaft 16. The attachment device 30 enables easy and ready mounting and simple exchange. If required the attachment device together with the drive shaft is removed from the driving device 12 and may be exchanged for a new one.

In FIG. 4 the internal diameter 32 of the rotor 22 21 is shown. The external diameter 34 of the rotor 22 corresponds to the internal diameter of the stator 21.

The internal diameter 32 is a multiple of the external diameter 28 of the drive shaft 16 so that the drive motor 20 can transmit high rotational forces.

FIG. 5 shows the drive motor of the agitating device absent an attachment device in a section. The back face shows the console accommodation 37 and the front face shows the end cover 35. A shaft opening 38 is provided in the end cover 35 to receive the drive shaft 16. The shaft opening 38 is provided with at least one shaft seal 39 to seal the drive motor toward the interior.

When the drive shaft 16 is inserted into the shaft opening 38, the external toothing 17 of the drive shaft 16 engages the internal toothing 27 of the tooth flange 26 of the coupling device 23. There is non-rotatable coupling between the drive shaft and the drive motor 20. The architecture showing a hollow rotor 22 having a large internal diameter 32 enables a lightweight structure for transmitting high rotational forces. Moreover, exchanging the drive shaft 16 does not require to open the drive motor 20.

FIGS. 6 and 6a show a front view respectively an enlarged, sectional front view of the drive motor 20 without the attachment device 30. The console accommodation 37 can be seen in the background while at the front the end cover 35 with the shaft opening 38 provided therein can be seen. One can see the tooth flange 26 with the internal toothing 27.

FIG. 6a shows an enlarged sectional view of a detail of the drive motor 20 showing a triangle segment of the stator 21 and the rotor 22. The stator 21 is provided with a number of windings 24 while permanent magnets 25 are disposed on the rotor 22. The number of windings is preferably larger than the number of permanent magnets and particularly preferably the permanent magnets and windings are more than 30 and particularly preferably more than 50 in number. The high number of windings and permanent magnets enable precise controlling, and high rotational force is enabled. In preferred configurations the drive motor 20 is configured as a torque motor. A preferred configuration e.g. provides for a minimum of 70 poles, 35 pole pairs and/or 280 magnets.

Figure 7:
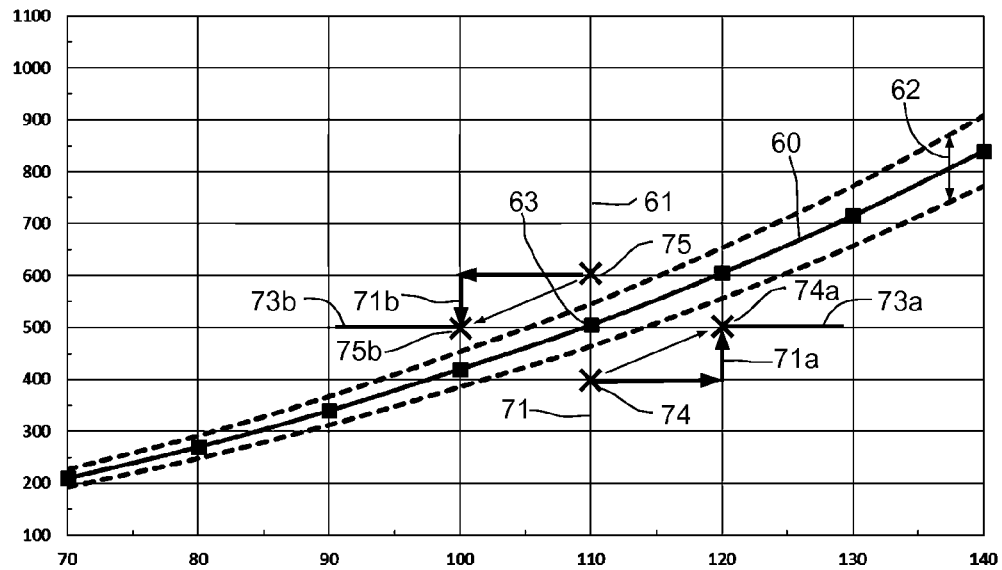
FIG. 7a target load curve for a given substrate.

FIG. 7 shows a target load curve 60 for a given substrate 7 and a tolerance range 62 showing a percentage extension around the target load curve 60. The tolerance range 62 may show a fixed value extension around the target load curve. A relative percentage of for example 5% or 10% deviation upwardly and downwardly is also possible.

In FIG. 7 the rotational force is plotted in Newton metres over the speed of rotation in revolutions per minute for a concrete case. This target load curve may be determined empirically and may apply for example to a specific substrate having a specific composition etc. This target load curve 60 is prescribed to enable specific control of the agitating device 10 respectively the agitating devices 10 via the control device 50.

As can be seen, the rotational force increases with increasing speed of rotation.

Controlling the digester 1 basically works in that at the start of the plant, a target load curve 60 is first prescribed or retrieved from a memory device. Thereafter the control device 50 prescribes a target speed of rotation 61. The control device 50 operates the agitating device 10 at an actual speed of rotation that corresponds at least roughly to the prescribed target speed of rotation. As the actual speed of rotation 71 is reached, an actual measurement value is captured at the operating point 74, 75 which value is characteristic of the torque or of the power of the agitating device 10 at the actual speed of rotation 71. For example an expansion measuring strip or the like on the drive shaft or in or at the rotor may serve to capture a measurement value that is characteristic of the rotational force applied. Or else it is possible and preferred to derive such measurement value 73a, 73b directly from the electric power consumption of the agitating device 10. The measurement value can be directly used as a characteristic value or the characteristic value is computed from the measurement value.

An actual characteristic value 74, 75 is derived from the measurement value. This actual characteristic value is compared against the target characteristic value 63 for the substrate ensuing from the target load curve 60 at the prescribed target speed of rotation 61.

If the control device determines that the rotational force occurring at the actual speed of rotation 71 lies outside the tolerance range 62 at the target speed of rotation 61, then either the actual speed of rotation is increased or else decreased a predetermined amount, depending on whether the actual rotational force is above or beneath the target characteristic value 63.

In the exemplary embodiment shown the actual speed of rotation 71 is increased or reduced in steps of 10 revolutions/min. It is also possible for the speed of rotation to be modified in smaller steps or else by percentage in dependence on the target speed of rotation 61.

After increasing the actual speed of rotation to the value 71a the actual measurement value and thus the actual characteristic value increases to the value 73a which in the presently selected exemplary embodiment lies within the tolerance range 62 around the target load curve 60 at the target speed of rotation 61. Due to the increase of the speed of rotation the rotational force has increased far enough for the rotational force to now lie in the desired range.

In the reversed case, i.e. if at the target speed of rotation 61 a rotational force is applied that lies above the tolerance range 62 of the target load curve 60, then the actual speed of rotation 71 is reduced to the actual speed of rotation 71b. Due to the lower speed of rotation the rotational force required also decreases so that the actual characteristic value 73b now, at the decreased actual speed of rotation 71b, lies within the tolerance range 62 of the target load curve 60 at the target speed of rotation 61.

Thus, in both cases—i.e. given a rotational force exceeding upwardly and downwardly—the actual rotational force is safely limited to within the desired range. Thereafter the remaining agitating cycle continues in the agitating device at the thus determined actual speed of rotation 71, 71a, or 71b.

In case that the increase or decrease of the actual rotational force in one step is not sufficient, the afore described loop is run iteratively until the actual rotational force lies in the desired target range.

This means that in the process flow a target load curve 60 is firstly lodged in the control device 50 or a target load curve 60 is retrieved from a memory device or from the control device 50 respectively.

The control device 50 prescribes a target speed of rotation as each agitating cycle begins, firstly the target speed of rotation 61. The control device 50 controls the agitating device 10 accordingly so that the agitating device 10 reaches an actual speed of rotation 71 corresponding to the prescribed target speed of rotation 61 in the scope of control accuracy. This results—depending on the substrate properties—in an operating point 74 or an operating point 75.

Thereafter the control device captures an actual measurement value 81 (see FIG. 8), which is characteristic of the torque of the agitating device 10 at the actual speed of rotation 71. The measurement value 81 is in particular the electric power consumption of the agitating device at the actual speed of rotation 71, although it may directly be the rotational force.

The control device 50 derives from the actual measurement value, taking into account the equipment factors, the losses occurring etc., an actual characteristic value of the rotational force applied. Or else the actual characteristic value may correspond to the power output at the actual speed of rotation since the rotational force can be computed from the output if the speed of rotation is known. In simple cases the actual characteristic value may correspond to the actual measurement value.

Thereafter the control device 50 compares the derived actual characteristic value 81 against the target characteristic value 63 resulting from the target load curve 60 at the prescribed target speed of rotation 61.

The control device 50 controls the agitating device 10 in dependence on the result of comparison.

The control device 50 determines in particular whether the actual characteristic value lies within a prescribed tolerance range 62 around the target load curve 60 at the target speed of rotation 61.

Thereafter, in the case of the operating point 74, namely if the actual characteristic value lies beneath the target characteristic value 63 and outside the tolerance range 62, the actual speed of rotation 71 of the agitating device 10 is increased a predetermined amount (presently, 10 revolutions/min) and a new operating point 74a ensues at the new actual speed of rotation 71a showing an actual rotational force 73a respectively a new actual characteristic value 73a.

Then the new operating point 74a lies within the prescribed tolerance range 62 of the target load curve 60 at the target speed of rotation 61 and the agitating cycle continues at this speed of rotation.

In the case of the operating point 75, namely if the pertaining actual characteristic value lies above the target characteristic value 63 and outside the tolerance range 62, then the actual speed of rotation 71 of the agitating device 10 is decreased a predetermined amount (presently, 10 revolutions/min) and a new operating point 75b ensues at the new actual speed of rotation 71b showing an actual rotational force 73b respectively a new actual characteristic value 73b.

Now the new operating point 75a also lies within the prescribed tolerance range 62 of the target load curve 60 at the target speed of rotation 61 and the agitating cycle continues at this speed of rotation 71b.

Figure 8:
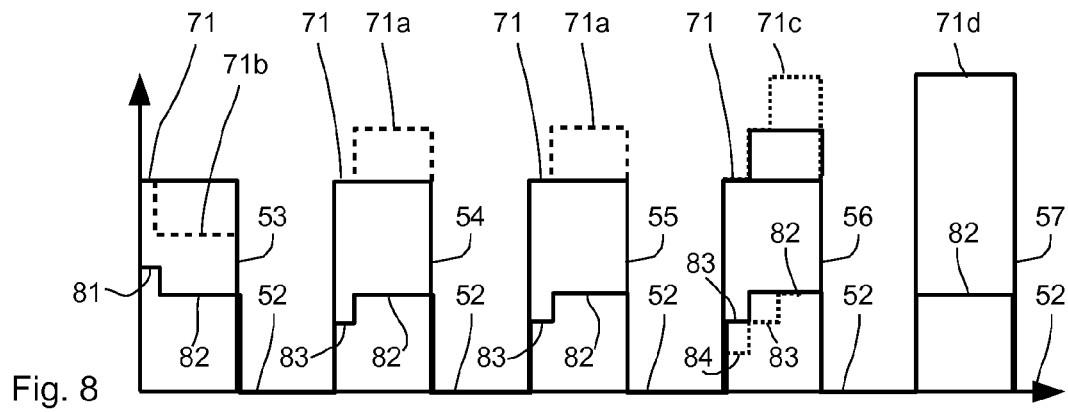
FIG. 8 the speed of rotation of the agitating device over time.

FIG. 8 shows a schematic time control curve for illustrating this principle. The speeds of rotation 71, 71a, 71b, 71c and 71d of the agitating device 10, the measurement values 81 to 84 and the characteristic values or rotational forces 91 to 94 over time resulting from the electric power consumption are plotted. A number of agitating cycles 53 to 57 interrupted by agitating stops 52 are illustrated.

At the beginning of the agitating cycle 53 the agitating device 10 is firstly controlled or operated at an actual speed of rotation 71 corresponding to the target speed of rotation 61. Since the measured electric output 81 respectively the resulting rotational force 91 and thus the characteristic value firstly lies above the desired target characteristic value, the actual speed of rotation is decreased to the value 71b so that the electric power consumption 82 decreases, resulting in a suitable torque respectively characteristic value 92 which now lies within the desired range. Then this speed of rotation 71b is maintained until the agitating cycle 53 ends.

The characteristic value 91 and the measurement value 81 (e.g. the power) may be linked linearly or by way of another formula. It is also possible to directly use the measurement values 81 to 84 for the characteristic values 91 to 94 if an unambiguous and reproducible association is given.

The agitating cycle 53 is followed by a rest cycle 52 in which the speed of rotation of the agitating device 10 is decreased to zero.

The following agitating cycle 54 then starts again at the actual speed of rotation 71 which corresponds to the target speed of rotation 61. In the agitating cycle 54 the electric power consumption 83 and thus the characteristic value respectively the torque 93 is firstly beneath the target value so that the speed of rotation is increased to the actual speed of rotation 71a. Thereafter the power consumption 82 and the rotational force 92 respectively the actual characteristic value 92 lie in the desired range. In the shown example the rotational force is computed from the power consumption with the speed of rotation.

The next rest cycle is followed by an agitating cycle 55 which in turn starts at the actual speed of rotation 71 which corresponds to the target speed of rotation 61. In this agitating cycle the power consumption 83 and thus the rotational force 93 detected is again too low so that the speed of rotation is increased to the actual speed of rotation 71a at which the desired actual rotational force 92 is applied.

In the next agitating cycle 56 the behaviour may be identical as is illustrated by the unbroken line. Or else it is possible that the properties of the substrate 7 have changed and a further increase of the actual speed of rotation to a still higher value 71c is required as is illustrated by the broken line. The variant shown in the broken line in the agitating cycle 56 requires an increase of the actual speed of rotation to the values 71a and 71c in two steps until the desired rotational force is obtained. Firstly the measurement value 84 and the pertaining characteristic value 94 are too low, then they increase to the measurement value 83 respectively the characteristic value 93 and only as the speed of rotation is increased to the value 71d do they reach the measurement value 82 and the desired rotational force respectively the characteristic value 92.

Every time the actual speed of rotation needs to be increased in successive agitating cycles a first counter 65 (see FIG. 1) is increased so that in the fourth agitating cycle 56 the counter shows the value 3. As a prescribed threshold 67 of e.g. 3, 5 or 10 or the like is exceeded, a new start value for the target speed of rotation is prescribed in the agitating cycle 57 following next. The new target value is then directly higher than the preceding value. This is exemplarily illustrated in FIG. 8 in the last agitating cycle in which an actual speed of rotation 71d is set.

If reversely the actual speed of rotation is decreased, a second counter 66 is increased. If it exceeds a threshold 67 (the same or different), there will be a suitable response.

If the first counter 65 or the second counter 66 exceeds a threshold 67 since displacements in the same direction had been required in successive agitating cycles, in particular instructions for action are issued such as feed more or less (depending on the direction), or another agitator position is selected, or longer (or shorter) agitating cycles are performed.

Figure 9:
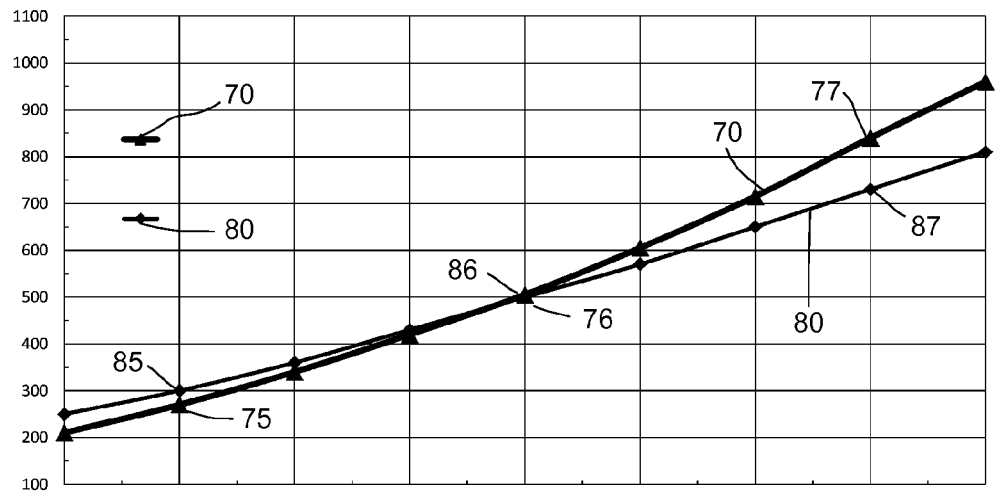
FIG. 9 an illustration of two different, captured load curves.

FIG. 9 shows two different load curves 70 and 80, with the rotational force plotted in Newton metres (Nm) over the speed of rotation in revolutions per minute.

The load curves 70 and 80 represent two different substrates 7 showing the load curve 70 for the material "liquid pig manure" and representing a low-viscosity medium. The load curve 80 was captured using the medium fermentation residue of a digester. This substrate for the curve 80 represents medium-viscosity matter.

In this exemplary embodiment the two load curves 70 and 80 intersect at the measuring points 76 and 86 while in the measuring point 75 the required rotational force of the load curve 70 is lower than the respective rotational force in the measuring point 85 of the load curve 80.

While in this exemplary embodiment, given the illustrated load curves 70 and 80, the rotational force required for rotation is firstly higher in the load curve 80 at low speeds of rotation (measuring points 75, 85), the rotational force required for rotating the agitating device 10 at higher speeds of rotation decreases in the load curve 80 relative to the load curve 70.

This means that the digester 1 and the agitating device 10 disposed therein allow to take up load curves 70, 80 of the substrate 7 present therein. The torque path of the load curves 70 or 80 allows to draw conclusions about the prevailing properties and optionally the composition of the substrate 7 concerned.

For example the load curve 70 may represent the target load curve for the substrate 7 used. Now if during operation a load curve with the agitating device and the control device 50 is recorded and the recorded load curve corresponds to the load curve 80, then the differences between the load curves 70 and 80 may be evaluated and concrete recommendations for action can be issued or directly initiated for adapting the load curve present in the substrate to the target load curve. For example the composition of the matter supplied may be changed. It is also possible to change the operating conditions of the agitating devices and for example to increase, or optionally decrease, the intensity of agitating for a specific time period. It is also possible to change the gas offtake in dependence on the captured load curves.

It is also possible and preferred to control the agitating device 10 in dependence on the desired gas offtake. For example higher sums of money for delivered power may be paid during specific times so as to provide an incentive to produce more gas and in particular electric power during these times. Thus, selective use of the agitating devices may take care that at, or prior to (for storage), those times, gas output is increased.

The agitating devices which are disposed for automatic displacement along the height of the support units 8 also allow to take up load curves 70, 80 of the substrate 7 located in the digester interior at different height positions 41, 42 etc. Different load curves 70, 80 at different heights allow conclusions about the presence and size of floating sludge layers and further parameters of the substrate. For example if low viscosity is detected at certain height layers, this may be indicative of certain components floating upwardly or other components settling down. Suitable measurements in layers above and below thus allow conclusions of an inhomogeneous distribution in the substrate in the digester.

Suitable controlling of the agitating devices 10 (height, angle, intensity) may achieve more complete thorough mixing.

Controlled strategies for expelling gas are possible, such as a helical automatic arrangement where expelling takes place from bottom to top.

The recording of load curves 70, 80 also allows to replace at any time the target load curve lodged in the control device 50 by a currently captured load curve. When the operator or the manufacturer finds that the digester 1 behaves as desired in the present operation, a new target load curve 60 may be created and stored. This may be provided on a regular basis or only as required, for example as the composition of the supplied substrate changes.

On the whole the invention provides an agitator technology dependent on the medium where automatic control is provided in dependence on the currently prevailing conditions of the substrate.

Operation is carried out so as to be energy saving. Controlling homogenises the substrate. The target values ensue from the medium employed. The state of the medium is captured locally.

The measurement and control values allow to issue measures for action. Deviations are captured and corrective measures are carried out or suggested. In case of incidents, measures for action are suggested. On the whole, complete monitoring and remote system diagnostics are possible. Servicing may be provided on site.

The agitator used is a highly efficient, gearless agitator having a low-loss direct drive ensuring a speed of up to 1000 Nm that is constant over the speed of rotation. The speed range of rotation is continuous, extending from 0-250 revolutions per minute.

The output range in the device described in the exemplary embodiment is 4 to 12.5 kW. The volume flow is up to 153 m3/min. The comfortable height adjusting and swivelling device achieves safe positioning as to height and angles.

Controlling may be done by means of a multifunction control of the process data such as volume flow, pressure, torque, power, SET parameter curve, parameter curve function.

While a particular embodiment of the present stirrer unit for a fermenter in a biogas plant has been described herein, it will be appreciated by those skilled in the art that changes and modifications may be made thereto without departing from the invention in its broader aspects and as set forth in the following claims.

LIST OF REFERENCE NUMERALS

| | |
|---|---|
| 1 | digester |
| 2 | digester wall |
| 3 | digester interior |
| 4 | horizontal |
| 5 | digester roof |
| 6 | servicing opening |
| 7 | substrate |
| 8 | support unit |
| 9 | cable |
| 10 | agitating device, agitator |
| 11 | housing |
| 12 | driving device |
| 13-15 | agitator blade |
| 16 | drive shaft |
| 17 | external toothing |
| 18 | engaging dog |
| 19 | blade hub |
| 19a | fixing unit |
| 20 | drive motor |
| 21 | stator |
| 21a | external diameter 21 |
| 22 | rotor |
| 23 | coupling device |
| 24 | winding |
| 25 | permanent magnet |
| 26 | tooth flange |
| 27 | internal toothing 26 |
| 28 | external diameter 16 |
| 29 | external diameter 19 |
| 30 | attachment device |
| 31 | bearing device 30 |
| 32 | internal diameter 22 |
| 33 | hollow portion of 22 |
| 34 | external diameter 22 |
| 35 | end cover |
| 36 | console |
| 37 | console accommodation |
| 38 | shaft opening |
| 39 | shaft seal |
| 40 | platform |
| 41 | 1st height position |
| 42 | 2nd height position |
| 50 | control device |
| 51 | frequency converter |
| 52 | rest cycle |
| 53-57 | agitating cycle |
| 60 | target load curve |
| 61 | target speed of rotation |
| 62 | tolerance range |
| 63 | target characteristic value |
| 65 | first counter |
| 66 | second counter |
| 67 | threshold |
| 70 | load curve |
| 71 | actual speed of rotation |
| 71a, 71b | actual speed of rotation |
| 72a, 72b | actual measurement value |
| 73a, 73b | actual characteristic value |
| 74, 74a | operating point |
| 75, 75a | operating point |
| 81-84 | measurement value |
| 91-94 | characteristic value |
| 100 | biogas plant |

The invention claimed is:

1. Agitating device in particular for a digester of a biogas plant having a housing and a driving device for rotatably driving at least one agitator blade, the driving device comprising a drive shaft and an electric drive motor, wherein the drive motor is accommodated sealed in the housing, wherein the drive motor comprises an outer, hollow stator and a rotary rotor which is configured at least partially hollow and is centrally accommodated therein, wherein the rotor is rotatably supported at the housing and comprises a coupling device for non-rotatable coupling with the drive shaft to drive the at least one agitator blade by means of the drive shaft, wherein the drive motor is configured as a direct drive and the drive shaft is coupled gearless with the drive motor, and wherein the internal diameter of the hollow part of the rotor is at least twice the size of the external diameter of the drive shaft, and wherein the coupling device of the rotor comprises a tooth flange which comprises an internal toothinq to non-rotatably receive the drive shaft equipped with an external toothinq.

2. The agitating device according to claim 1 wherein the stator is equipped with a plurality of electric windings and the rotor, with a plurality of permanent magnets.

3. The agitating device according to claim 1 wherein the driving device comprises an attachment device having a bearing device to rotatably support the drive shaft wherein the attachment device is detachably connected with the housing.

4. The agitating device according to claim 1 wherein a blade hub is non-rotatably disposed on the drive shaft and the agitator blade is attached to the blade hub.

5. The agitating device according to claim 4 wherein the drive shaft comprises at least one radial engaging dog for non-rotatable connection with the blade hub.

6. The agitating device according to claim 4 wherein the blade hub is axially fixed to the front end of the drive shaft by means of a fixing unit.

7. The agitating device according to claim 4 wherein the external diameter of the blade hub is at least twice the size of the external diameter of the drive shaft.

8. The agitating device according to claim 1 wherein the external diameter of the rotor is at least three times the size of the external diameter of the drive shaft.

9. The agitating device according to claim 4 the external diameter of the rotor is larger than the external diameter of the blade hub.

10. The agitating device according to claim 1 wherein the outer face of the stator forms an outside surface of the housing.

11. The agitating device according to claim 1 wherein the drive shaft protrudes from a front side of the housing and wherein a console accommodation for attachment to a console is disposed on the rear face of the housing.

12. The agitating device according to claim 1 wherein the drive shaft extends out of the housing outwardly from the tooth flange through a shaft opening in an end cover wherein at least one shaft seal is disposed on the shaft opening between the end cover and the drive shaft.

13. The agitating device according to claim 1 wherein a plurality of two, three or more agitator blades is provided.

14. Digester of a biogas plant having a digester interior that can be filled at least partially with a substrate wherein at least one agitating device controlled by a control device is disposed in the digester interior, the agitating device comprising a housing, at least one agitator blade and a driving device to rotatably drive the at least one agitator blade, the driving device comprising a drive shaft and an electric drive motor which drive motor is accommodated sealed in the housing, wherein the drive motor comprises an outer, hollow stator and a rotary rotor which is configured at least partially hollow and is centrally accommodated therein, wherein the rotor is rotatably supported at the housing and comprises a coupling device for non-rotatable coupling with the drive shaft to drive the at least one agitator blade by means of the drive shaft, wherein the drive motor is configured as a direct drive and the drive shaft is coupled gearless with the drive motor, and wherein the internal diameter of the hollow part of the rotor is at least twice the size of the external diameter of the drive shaft, and wherein the coupling device of the rotor comprises a tooth flange which comprises an internal toothinq to non-rotatably receive the drive shaft equipped with an external toothinq.

15. The digester according to claim 14 wherein the rotor is provided inside and the stator surrounds the rotor.

16. The digester according to claim 14 wherein the driving device is controlled by a frequency converter.

17. The digester according to claim 14 wherein the drive motor is suitable, given a speed of 1 revolution/second, to apply a torque of at least 250 Nm.

18. The digester according to claim 14 wherein the drive motor is configured for speeds of rotation of up to 150.

19. The digester according to claim 14 wherein the agitating device is automatically height-adjustable and/or side-adjustable.

* * * * *